US009706916B2

(12) United States Patent
Kersting et al.

(10) Patent No.: US 9,706,916 B2
(45) Date of Patent: *Jul. 18, 2017

(54) APPARATUS FOR MONITORING ONE OR MORE SURGICAL PARAMETERS OF THE EYE

(71) Applicant: Novartis AG, Basel (CH)

(72) Inventors: Oliver Kersting, Kleinmachnow (DE); Martin Grunding, Rangsdorf (DE)

(73) Assignee: Novartis AG, Basel (CH)

( * ) Notice: Subject to any disclaimer, the term of this patent is extended or adjusted under 35 U.S.C. 154(b) by 350 days.

This patent is subject to a terminal disclaimer.

(21) Appl. No.: 14/352,137

(22) PCT Filed: Oct. 22, 2012

(86) PCT No.: PCT/EP2012/070850
§ 371 (c)(1),
(2) Date: Apr. 16, 2014

(87) PCT Pub. No.: WO2013/057307
PCT Pub. Date: Apr. 25, 2013

(65) Prior Publication Data
US 2014/0243623 A1    Aug. 28, 2014

(30) Foreign Application Priority Data

Oct. 22, 2011    (EP) .................................... 11186271

(51) Int. Cl.
*A61B 5/00*    (2006.01)
*A61B 3/10*    (2006.01)
(Continued)

(52) U.S. Cl.
CPC ............ *A61B 3/113* (2013.01); *A61B 3/0025* (2013.01); *A61B 3/1005* (2013.01); *A61B 3/107* (2013.01);
(Continued)

(58) Field of Classification Search
CPC ... A61F 9/007; A61F 2/14; A61F 2/16; A61B 3/0025; A61B 5/4851; A61B 3/107; A61B 3/113; A61B 3/14; A61B 3/1005
See application file for complete search history.

(56) References Cited

U.S. PATENT DOCUMENTS 4,761,071 A * 8/1988 Baron .................... A61B 3/107
351/212
5,416,317 A * 5/1995 Nishimura ............. G03B 13/02
250/221

(Continued)

FOREIGN PATENT DOCUMENTS

CN        1166128        11/1997
CN        1518948        8/2004
(Continued)

OTHER PUBLICATIONS

English translation of Japanese Office Action issued for JP 2014-536276 dated Jun. 2, 2015, 8 pgs.
(Continued)

*Primary Examiner* — Kim Vu
*Assistant Examiner* — Pinalben Patel

(57) ABSTRACT

An apparatus for monitoring one or more surgical parameters of the eye over multiple sessions which are temporally spaced apart and between which the eye of the patient can have moved, said apparatus comprising: a camera for taking one or more images of the eye; a module for determining during a first session said at least one surgical parameter of the eye and its coordinates based on the image taken by said camera in a first coordinate system; a module for determining during a second session temporally spaced apart from said first session said at least one surgical parameter of the eye and its coordinates based on the image taken by said camera in a second coordinate system; a module for determining the eye motion in six degrees of freedom between (Continued)

said first and said second session and for determining a coordinate transformation based thereon; a module for transforming based on said determined eye motion said at least one surgical parameter of the eye and its coordinates from said first coordinate system into said second coordinate system; a module for quantifying and/or visualizing the change of said at least one surgical parameter of the eye and its coordinates between said first and said second session based on said surgical eye parameter and its coordinates measured during said second session and said transformed surgical eye parameter and its coordinates measured during said first session, wherein said surgical eye parameters are one or more of the following: implant-related parameters of the eye which are based on an implant which has been surgically placed in the eye of a patient; or the location and/or contour of corneal or limbal or scleral incisions.

16 Claims, 15 Drawing Sheets

(51) Int. Cl.
| | |
|---|---|
| A61B 3/113 | (2006.01) |
| A61B 3/107 | (2006.01) |
| A61B 3/14 | (2006.01) |
| A61F 2/14 | (2006.01) |
| A61F 9/007 | (2006.01) |
| A61B 3/00 | (2006.01) |
| A61F 2/16 | (2006.01) |

(52) U.S. Cl.
CPC ............. *A61B 3/14* (2013.01); *A61B 5/4851* (2013.01); *A61F 2/142* (2013.01); *A61F 9/007* (2013.01); *A61F 2/14* (2013.01); *A61F 2/16* (2013.01)

(56) References Cited

U.S. PATENT DOCUMENTS

| | | | | |
|---|---|---|---|---|
| 8,360,580 | B2* | 1/2013 | Chauveau | A61B 3/111 351/204 |
| 8,709,078 | B1* | 4/2014 | Friend | A61F 2/14 623/5.11 |
| 9,125,559 | B2* | 9/2015 | Kersting | A61B 3/1005 |
| 9,237,844 | B2* | 1/2016 | De Bruijn | A61B 3/113 |
| 2003/0123027 | A1* | 7/2003 | Amir | G06K 9/00604 351/209 |
| 2003/0223037 | A1* | 12/2003 | Chernyak | A61B 3/1015 351/209 |
| 2004/0070730 | A1* | 4/2004 | Mihashi | A61B 3/107 351/221 |
| 2004/0254441 | A1* | 12/2004 | Schrunder | A61B 3/0025 600/407 |
| 2004/0263785 | A1* | 12/2004 | Chernyak | A61B 3/1015 351/246 |
| 2005/0024586 | A1* | 2/2005 | Teiwes | A61B 3/113 351/209 |
| 2007/0171369 | A1 | 7/2007 | Grundig | |
| 2009/0171305 | A1* | 7/2009 | El Hage | A61F 2/14 604/294 |
| 2013/0208241 | A1* | 8/2013 | Lawson | A61B 3/0091 351/206 |
| 2013/0308098 | A1* | 11/2013 | Levecq | A61B 3/1015 351/206 |
| 2013/0345807 | A1* | 12/2013 | Olsen | A61B 3/0025 623/6.11 |
| 2014/0368792 | A1* | 12/2014 | Friedman | A61B 3/107 351/206 |
| 2015/0066466 | A1* | 3/2015 | Chernyak | A61B 3/028 703/11 |
| 2015/0077528 | A1* | 3/2015 | Awdeh | G06T 11/00 348/53 |

FOREIGN PATENT DOCUMENTS

| | | |
|---|---|---|
| CN | 101677762 | 8/2012 |
| EP | 2184005 A1 * | 5/2010 |
| JP | H06-230271 | 8/1994 |
| WO | WO2006101943 | 9/2006 |

OTHER PUBLICATIONS

International Search Report issued for PCT/EP2012/070850 dated Apr. 25, 2013, 4 pages.

English translation of Chinese Office Action issued for CN 201280051841.4 dated Aug. 19, 2015, 8 pgs.

* cited by examiner

APPARATUS FOR MONITORING ONE OR MORE SURGICAL PARAMETERS OF THE EYE

CROSS-REFERENCE TO RELATED APPLICATIONS

This application is a United States national phase application of co-pending international patent application number PCT/EP2012/070850, filed Oct. 22, 2012, which claims priority to European Application No. 11186271.0, filed Oct. 22, 2011, the disclosures of which are incorporated herein by reference.

FIELD OF THE INVENTION

This Invention relates to an apparatus for monitoring one or surgical parameters of the eye.

BACKGROUND OF THE INVENTION

The invention refers to the field of ophthalmology, specifically refractive eye diagnostic and eye surgery. For most refractive eye treatments (1) pre-surgery diagnostic information of the patient's eye is determined to choose the adequate procedure (e.g. implant vs. laser) and define the individual treatment steps (e.g. where to cut or how to align the implant), (2) the individual surgery treatment is performed inserting refraction correcting implants (e.g. IOL's, corneal inlays) or executing surgery actions (e.g. cut incisions, apply laser shot patterns) and (3) post-surgery diagnostic information of the patient's eye including implant and/or surgery action is determined.

(1) and (3) are typically performed outside the operation room using diagnostic devices like keratometer, topographer, wavefront analyzer, scheimflug devices, interferometer or slit lamps. (2) is typically performed in the operation room using a general purpose surgical microscope and adequate tools to support the surgeons manual work (e.g. knifes, phaco machine) or using dedicated devices for partial or full automation of surgical steps (e.g. refractive excimer laser treatment, cataract laser treatment).

Currently there is a wide range of diagnostic devices that measure properties of the eye. A topograph or keratometer determines the shape and curvature of the patient's cornea (e.g. Zeiss Atlas), a wavefront device determines the full refraction of the patient's eye optics (e.g. AMO Wavefront Sciences COAS), an interferometer measures the axial length of the patient's eye ball (e.g. Haag-Streit LenStar LS900), a scheimflug device measures the front-side and back-side of the corneal refraction as well as the thickness (e.g. Oculus Pentacam) and a slit lamp provides an image of the patient's front of the eye for manual examination by the doctor.

All different diagnostic approaches and associated devices evolved to accurate tools with a high repeatability for single eye measurements and therefore are applied pre-surgery as well as post-surgery for examination to verify clinical outcome.

There are further approaches appearing on the ophthalmology landscape for intra-surgery measurement of the eye. An intra-surgery keratometry hand tool (e.g. astigmatic ruler by STORZ) can be used to roughly measure the corneal shape and its changes during the surgery, an intra-surgery wavefront device—in principle—allows the determination of the required power and astigmatism of an artificial lens after the removal of the natural lens (e.g. Wavetec ORange). All intra-surgery refraction measurement tools suffer from the moment of taking the measurement: The moment of eye surgery. Intra-surgery the eye properties are changed compared to the natural no-surgery condition. The intra ocular pressure might be higher, the cornea might be deformed due to mechanical impacts, the refraction of eye fluids changed due to partial exchange of fluids, etc. But independent from this general drawback, the repeatability of those devices in one moment on one specific eye is reasonable.

All named devices and tools in this section above have in common the availability of a more or less consistent intra-device coordinate system ("device-consistent" which means that the tool or device provides from a patient X measured at one moment T multiple times a consistent output) but they all lack a full process covering consistent coordinate system ("process-consistent"). With a process-consistent coordinate system every process step (measurement or treatment) where the patient's eye is visually acquired, can be matched and transformed to an initially defined reference coordinate system.

Due to the lack of a process-consistent coordinate system, systematic errors that occur between different steps are directly impacting the overall treatment error. Some examples:

a) Sit-to-Sit-Error: Current practice is making all diagnostic measurements with the patients head is in an upright position. The assumption of 99% of surgeons is that the gravitation keeps the eye in the exact orientation for every measurement. This way a combination of measurement results from different devices can easily be performed. Unfortunately this assumption is wrong. The eye can rotate up to 7° from one sitting position to another.

b) Marker-Error: Current practice is the use of ink markers or ink marker tools for marking axes or positions on the cornea or the limbus border. The accuracy for using ink markers is limited due to the size of the marker (e.g. can be a 5° thick mark), the unknown coordinate system while the surgeon is doing the marking (see a)) as well as the accuracy of reading a marker. The errors can easily sum up to 6° or more.

c) Surgeons-Error: Till now e.g. the cataract surgeon is doing most surgery steps that require special accuracy fully manual: They position incisions or align implants based on the marks they did previously. Besides the Maker Error the mechanical precision of the surgeon fingers needs to be taken into account.

d) Implant-Error: Depending on the type of implant different post-surgery movements of the implant are likely to occur. For example early toric IOL designs tend to move post-operatively up-to 10° based on slit lamp assessment.

Deriving guidelines, nomograms or new implant designs and tool designs from the overall clinical outcome a separation of different systematic error influences like a)-d) could not be determined or distinguished.

With the high optical complexity of latest generation implants or latest generation laser systems this demand for more diagnostic and surgery accuracy is already present, but with existing tools only overall errors can be determined but no error propagation addressing every single diagnostic step or surgery step.

SUMMARY OF THE INVENTION

In view of the foregoing situation, according to one embodiment there is provided a process-consistent coordinate system every process step (measurement or treatment)

where the patient's eye is visually acquired, can be matched and transformed to an initially defined reference coordinate system. This overcomes the disadvantages of the lack of a coherent process coordinate system over multiple sessions which may comprise pre-surgery, surgery and post surgery.

According to one embodiment an apparatus is provided for monitoring one or more surgical parameters of the eye of a patient over multiple sessions which are temporally spaced apart and between which the eye of the patient can have moved, said apparatus comprising:

a camera for taking one or more images of the eye;

a module for determining during a first session said at least one surgical parameter of the eye and its coordinates based on the image taken by said camera in a first coordinate system;

a module for determining during a second session temporally spaced apart from said first session said at least one surgical parameter of the eye and its coordinates based on the image taken by said camera in a second coordinate system;

a module for determining the eye motion in six degrees of freedom between said first and said second session and for determining a coordinate transformation based thereon;

a module for transforming based on said determined eye motion said at least one surgical parameter of the eye and its coordinates from said first coordinate system into said second coordinate system;

a module for quantifying and/or visualizing the change of said at least one surgical parameter of the eye and its coordinates between said first and said second session based on said surgical eye parameter and its coordinates measured during said second session and said transformed surgical eye parameter and its coordinates measured during said first session, wherein said surgical eye parameters are one or more of the following:

implant-related parameters of the eye which are based on an implant which has been surgically placed in the eye of a patient; or the location and/or contour of corneal or limbal or scleral incisions.

Such an arrangement allows to monitor surgical parameters even after the surgery has been performed to check whether there has been any temporal change of the surgical parameters like implant-related eye parameters or the location or contour of incisions. This is an important diagnostic information for monitoring the success or failure of surgery during the post-surgical phase.

According to one embodiment said implant related eye parameter comprises one or more of the following:

the orientation and/or position of the implant in the eye;
the location and/or the contour of the rhexis;
the overlap of the rhexis with the contour of the implant.

These are preferable examples of implant-related parameters for which it is interesting to monitor them to watch the surgical result over time.

According to one embodiment said module for quantifying and/or displaying the change of said at least one surgical eye parameter comprises:

A module for displaying said least one surgical eye parameter measured during said second session and said transformed surgical eye parameter measured during said first session in the image of the eye taken during said second session; and/or a module for calculating the difference between said surgical eye parameter measured during said second session and said transformed surgical eye parameter measured during said first session and for visualizing said difference in said image of the eye taken during said second session.

This enables the comparison of the development of a surgical parameter over time, e.g. by comparing a post-surgical change with the situation during surgery, or by comparing two different post-surgical instances in time while the eye movement between the two measurements is compensated. The surgical parameter (like the location of the implant) as determined at the two instances of time may be directly visualized by displaying it in the image with the eye motion being compensated, or there may be calculated a difference (like a difference in x-, y- or rotation parameters) and just the difference being displayed in the image.

According to one embodiment said first session is a pre-surgery session and said second session is an intra surgery session or a post surgery session, or said first session is an intra-surgery session and said second session is a post surgery session, or said first session is a post-surgery session and said second session is another post surgery session performed at a later time. These are suitable examples of sessions at different instances of time for which the surgical parameters may be compared while compensating for the eye motion between the sessions.

According to one embodiment the apparatus further comprises:

A module for measuring and recording said at least one surgical eye parameter during multiple sessions over time in order to record the change of said at least one surgical eye parameter over time.

This enables the recording and monitoring of the development of surgical eye parameters and thereby of the surgical result over an arbitrarily long time period in a consistent coordinate system by compensating the eye motion. In this way e.g. studies regarding the long term success or failure of surgical techniques may be carried out which so far are not possible.

According to one embodiment the apparatus further comprises: an illumination unit for illuminating the eye by a ring-shaped light pattern to generate corneal reflection, said illumination unit being preferably located such that the center of the ring is coaxial with the optical axis of the camera;

a module for determining during said first and/or said second session the location of the corneal reflections in the image of the eye;

a module for determining during said first and/or said second session based on said determined location of the corneal reflections, at least one further parameter of the eye and its coordinates in said first and/or second coordinate system based on a geometrical model representing the eye as a spherical eyeball having a spherically shaped cornea mounted thereon; a module for visualizing said at least one further parameter of the eye together with said at least one implant related eye parameter in the same image after having transformed its coordinates based on the eye motion between said first and said second session so that the motion of the eye is compensated.

In this way further eye parameters which are not surgical eye parameters may be determined and monitored in addition to the surgical eye parameters. They may also be visualized additionally together with the surgical eye parameters while compensating for the eye motion between the sessions.

According to one embodiment said at least one further parameter is determined based on an eye model which represents the shape and location of the eye by a spherical eyeball and a cornea mounted thereon and having a spherical shape or the shape of an ellipsoid to thereby enable the calculation of said at least one further parameter using the measured location of said corneal reflections and said eye model.

This is a suitable way of determining eye parameters which are not directly measurable from the images taken by a camera.

According to one embodiment said at least one further eye parameter comprises one or more of the following:

a) the k-readings which define the shape of the cornea in terms of rotation ellipsoid parameters;

b) the line of sight as the line connecting the pupil center and a fixation point of known location;

c) the corneal chamber depth;

d) the visual axis of the eye;

e) the determination whether the eye is the left eye or the right eye. These are suitable examples of further eye parameters.

According to one embodiment said at least one further eye parameter comprises the k-readings which are measured by determining a best fit ellipse to the corneal reflections and determining the major axis, the minor axis and the orientation of the ellipse.

This enables the determination of astigmatism parameters including the length of the steep and flat axis of the cornea as well as the orientation of the astigmatism. The diameter of the best fit cornea sphere can be approximated by the mean of flat and steep axis.

According to one embodiment said apparatus further comprises a fixation target at known coordinates, preferably on the optical axis of the camera, and said at least one further eye parameter comprises the visual axis which is determined as the vector connecting the cornea center and the known fixation target, where the cornea center is determined based on the location of the corneal reflections.

This enables the determination of the visual axis. According to one embodiment said at least one further eye parameter comprises the angle kappa between the visual axis and the pupil axis, or said further parameter is the intersection point between the visual axis and the cornea surface, where the cornea radius is determined based on the location of said corneal reflections.

This allows the determination of further parameters which are interesting for the surgeon.

According to one embodiment said at least one further eye parameter comprises the anterior chamber depth which is determined based on determining the radius of the limbus RI and assuming it to be a circle of latitude on the best fit cornea sphere with radius Rc which is determined based on the corneal light reflections such that the corneal chamber depth CD is derived by CD=Rc−sqrt(Rc^2−RI^2).

The anterior chamber depth is an interesting information for the surgeon,

According to one embodiment said at least one further eye parameter comprises the line of sight which is determined as the vector connecting the pupil center and said fixation point of known location, with the z-coordinate of the pupil center being determined based on a known distance between camera and the eye and the x- and y-coordinates of the pupil being determined based on measuring the pupil location in the image, and/or said at least one further eye parameter comprises the pupillary axis being the line going through the center of the pupil and being orthogonal to the cornea surface.

Line of sight and papillary axis may be determined in this way.

According to one embodiment said at least one further eye parameter comprises the determination of whether the center of the limbus or the center of the cornea is closer to the optical axis of the camera when the patient fixates a known fixation point lying on the optical axis of the camera.

This enables the determination whether the eye is the left eye or the right eye. It may be used as a safeguard mechanism to prevent the surgery or diagnosis being performed on the wrong eye.

According to one embodiment the apparatus further comprises:

A module for visualizing an arbitrary combination of said at least one or more surgical eye parameters and said at least one or more further eye parameters determined during said first session and a possibly different arbitrary combination of said at least one or more surgical eye parameters and said at least one or more further eye parameters determined during said second session in the same image such that the eye motion between said first and second session is compensated.

This allows the visualization of any surgical or other parameters in any combination which are of interest while compensating for the eye motion between different sessions.

DETAILED DESCRIPTION

According to one embodiment there is provided an apparatus which enables a solution for monitoring eye properties related to eye surgery over time, between any two of the following:

pre surgery intra surgery post surgery

In the following there will be referred to spatial and refractive eye properties as "eye parameters".

For intra surgery measurements the solution according to one embodiment requires a microscope camera that is connected to a PC.

Figure 1:
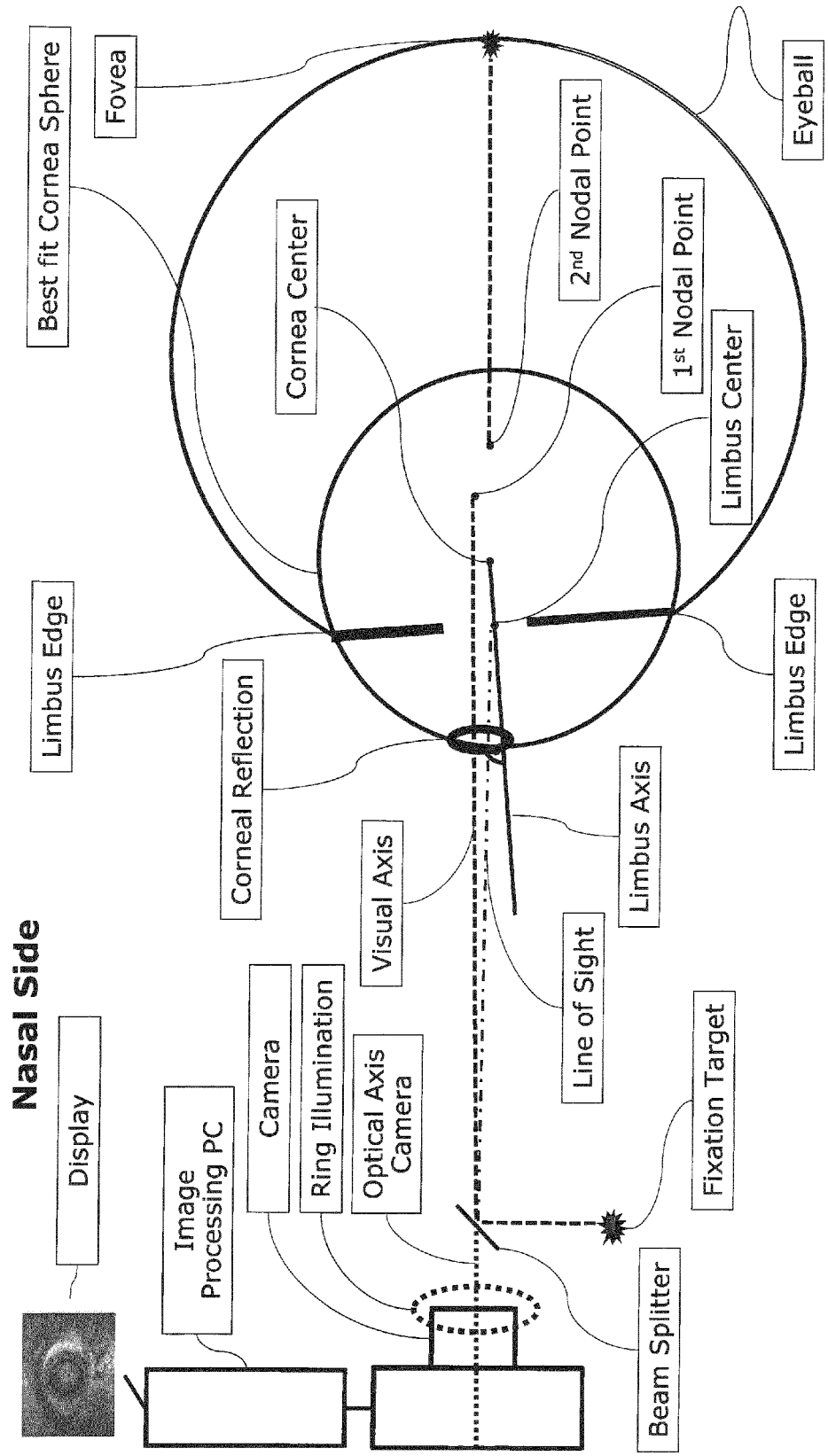
FIGS. 1 to 15 illustrate embodiments of the invention.

For pre and post surgery measurements according to one embodiment the solution described here uses a specific apparatus hereinafter called a 'Reference Device' (RD) which consists of a PC connected to a digital camera and an illumination system on a cross table which allows capturing a high resolution color image of a patients eye in a defined position. The apparatus according to one embodiment and its use in connection with an eye is schematically illustrated in FIG. 1.

The illumination system of the RD generates a ring-shaped illumination pattern and may e.g. consist of a concentric ring of LEDs around the optical axis of the camera and a fixation LED which is injected on the optical axis of the camera. Preferably the ring of LEDs is coaxial with the optical axis of the camera and the optical axis of the camera is orthogonal to the area of the ring.

The acquired images are processed on the PC and can be used to automatically or manually measure either absolute eye parameters as they are at the time of image acquisition or changes of eye parameters relative to a reference image of a previous measurement session.

According to one embodiment the apparatus allows determining the spatial relation of the measured parameters with respect to each other within and between measurement sessions by actively measuring how the eye did move in 6 degrees of freedom between 2 measurement sessions.

The eye motion in 6 degrees of freedom is according to one embodiment measured based on registration of scleral blood vessel features or limbus, iris features and corneal reflections of a defined illumination system between 2 sessions.

One initial (usually pre surgery, but post-surgery is also possible) reference measurement serves as a reference coordinate system for all subsequent measurement sessions (pre or post surgery) of the same eye.

All parameters measured in subsequent sessions can be transformed into the reference (or vice versa) coordinate system by applying a spatial similarity transformation that accounts for the eye motion between the current measurement and the reference measurement. Once transformed to the reference coordinate system the parameters from different measurements can be compared and the influence of eye motion is eliminated.

This approach is used in one embodiment for analyzing parameters like the position and the orientation of eye implants (e.g. IOLs) in the eye. This way it can be monitored how stable the implant is located and oriented in the eye over time without being limited in accuracy to the amount of eye motion between measurement sessions.

Typical eye parameters that may be measured with the RD in a pre surgery reference measurement session are:

1) Pupil position, shape and size (photopic, scotopic, mesopic)
2) Limbus position shape and size
3) K-readings
4) Line of sight (LOS)
5) Approximation of corneal chamber depth
6) Intersection of LOS with cornea surface and angle kappa
7) OD/OS classification These eye parameters may be measured in a pre-surgery session and then later in intra-surgery or a post-surgery session, and their change or development over time may then be determined and visualized.

The eye motion which then enables the transformation of the eye parameters from one session to another according to one embodiment is determined by measuring the following:

8) Relative eye motion with respect to the reference measurement by measuring
   a) Relative translations in X and Y
   b) Relative translation in Z
   c) Relative cyclotorsion (around Z axis)
   d) Relative roll and tilt (around X and Y axis)

Other parameters which relate to ophthalmic surgery and the placement of implants may be measured as well.

In a (subsequent) intra or post surgery measurement session the following eye parameters may be measured in addition to (or instead of) the aforementioned eye parameters:

9) Orientation and Position of implants in the eye
   a) Location of the implant markings in the eye (toric marks or multifocal rings)
   b) Rotational orientation of implants
   c) Roll and Tilt of implants
   d) Implant contour
   e) XY-Position of the implant center
   f) Location of the implant haptics in the eye.

Moreover, another type of parameters which is also related to implants may be measured, namely 10) The Rhexis in the capsular bag, specifically
   a) Contour
   b) Diameter
   c) XY Position in the eye
   d) Overlap with lens In an alternative instance the RD contains an additional Scheimpflug or interferometer setup that allows to measure inside the cornea and lens tissue. In such a setup in addition to the parameters mentioned above, corneal incisions can be measured in terms of location in the eye, width and depth as well as the distance of the implant to the cornea.

In a second alternative instance the RD also contains a placido ring illumination that allows to analyze the topography of the cornea. In such a setup the exact changes in corneal topography e.g. before and after LASIK laser treatment can be assessed. By applying the spatial similarity transformation to the topography data it is possible to ensure that the topography data is correctly aligned and changes in the topography of the cornea are being calculated correctly.

In a third alternative instance the RD also contains a wavefront analyzer (Hartmann-Shack-Sensor) that allows to analyze the full refraction of the eye.

In yet another alternative instance a registration of the image from the RD is performed to other dedicated eye diagnosis devices allowing to transform the dedicated parameters measured by these devices to the reference coordinate system provided by the RD. In this instance changes in these additional spatial eye parameters can also be monitored over time in the consistent reference coordinate system provided by the RD.

In the following embodiments of an apparatus according to the invention (a reference device) will be described and its operation and function will be explained.

The main functionality of the apparatus according to one embodiment is to:

measure multiple eye parameters or parameter sets in different measurement sessions.

determine the eye motion between the measurement sessions.

apply a spatial similarity transformation to transform each eye parameter or parameter set to the reference coordinate system defined by the initial reference measurement.

quantify and display changes in eye parameters or eye parameter sets between measurement sessions pre-, intra- and post-surgery.

quantify and display differences between surgery plan and post surgery outcome.

The eye parameters in one embodiment are measured by combining image processing with a generic eye model. For example, according to one embodiment the model represents the eyeball as a sphere with the cornea being also spherical (or in one embodiment having an ellipsoid shape) being mounted thereon. Using such an eye model allows to indirectly measure properties like the corneal chamber depth which is not directly visible in the image.

Now it will be explained how according to embodiments eye parameters are determined which may then be transformed from one session to the other using the detected eye motion 1) Pupil Position, Shape and Size (Photopic, Scotopic, Mesopic)

Pupil detection is a classic image processing task. A classic threshold based approach is used here. By varying the illumination intensity the pupil of the patient can be brought into a photopic, scotopic and mesopic condition (pupil size changes).

2) Limbus Position Shape and Size

Similar as for pupil detection a standard approach using limbal edge detection and a circular fit is used here.

3) K-Readings:

The k-readings define the shape of the cornea in terms of rotation ellipsoid parameters as minor axis (steep axis in ophthalmology) major axis (flat axis in ophthalmology) and axis orientation. Also here in one embodiment a well known keratometry approach is being applied by detecting the corneal reflections of the coaxial ring of LEDs of the RD. The best fit ellipse into these reflections gives the parameters of the k-readings.

4) Line of Sight (LOS)

Figure 2:
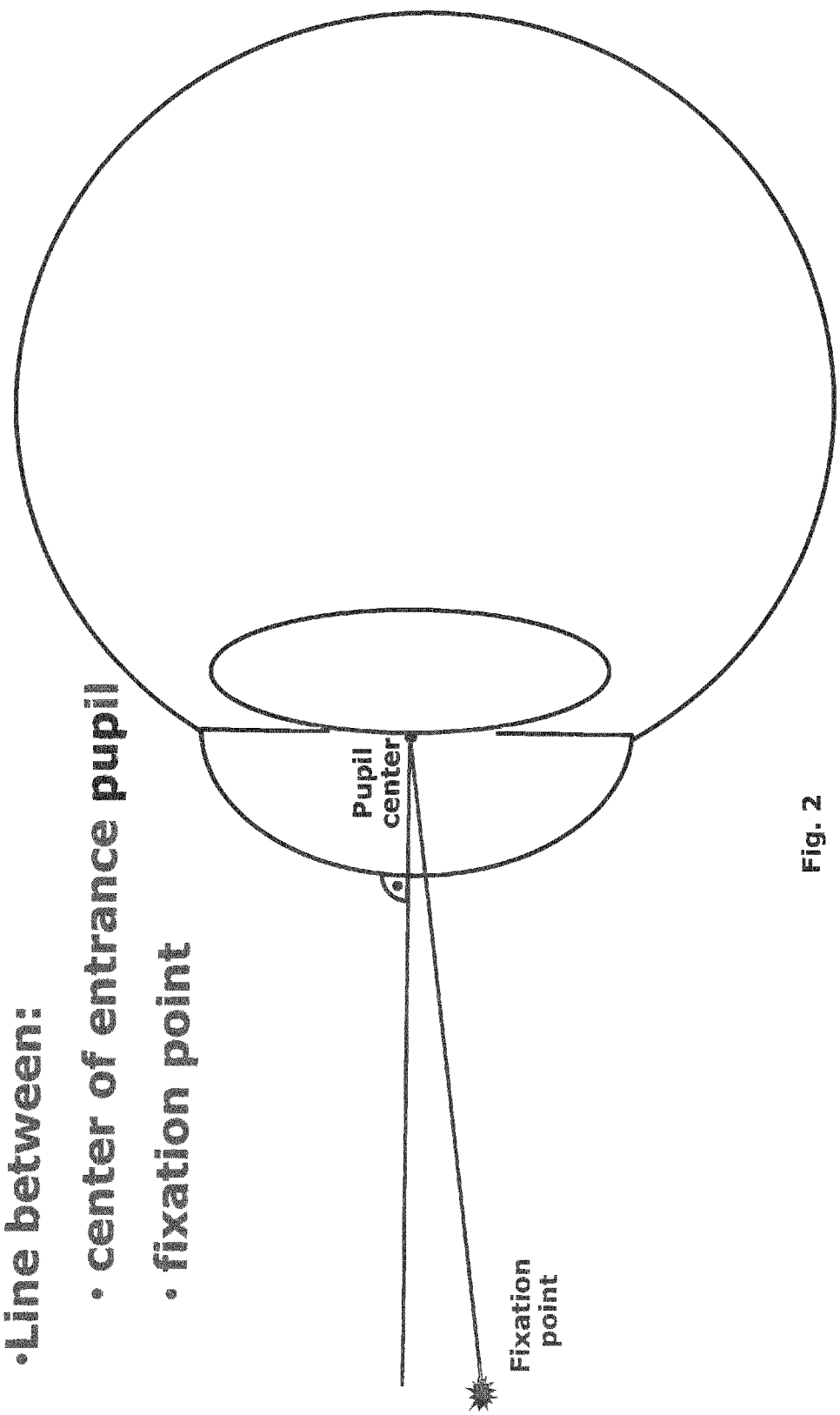

The Line of sight connects the fixation point with the center of the eye's entrance pupil. The RD takes an image from a defined distance Zp to the eye. By design the imaging geometry of the camera is known as well as the position of the fixation target with respect to the projection center of the camera. The pupil can therefore be measured in 3 dimensions with its coordinates Xp, Yp and Zp. The 3d vector connecting the entrance pupil and the fixation target gives the LOS. This is schematically illustrated in FIG. 2.

5) Approximation of Corneal Chamber Depth

Figure 3:
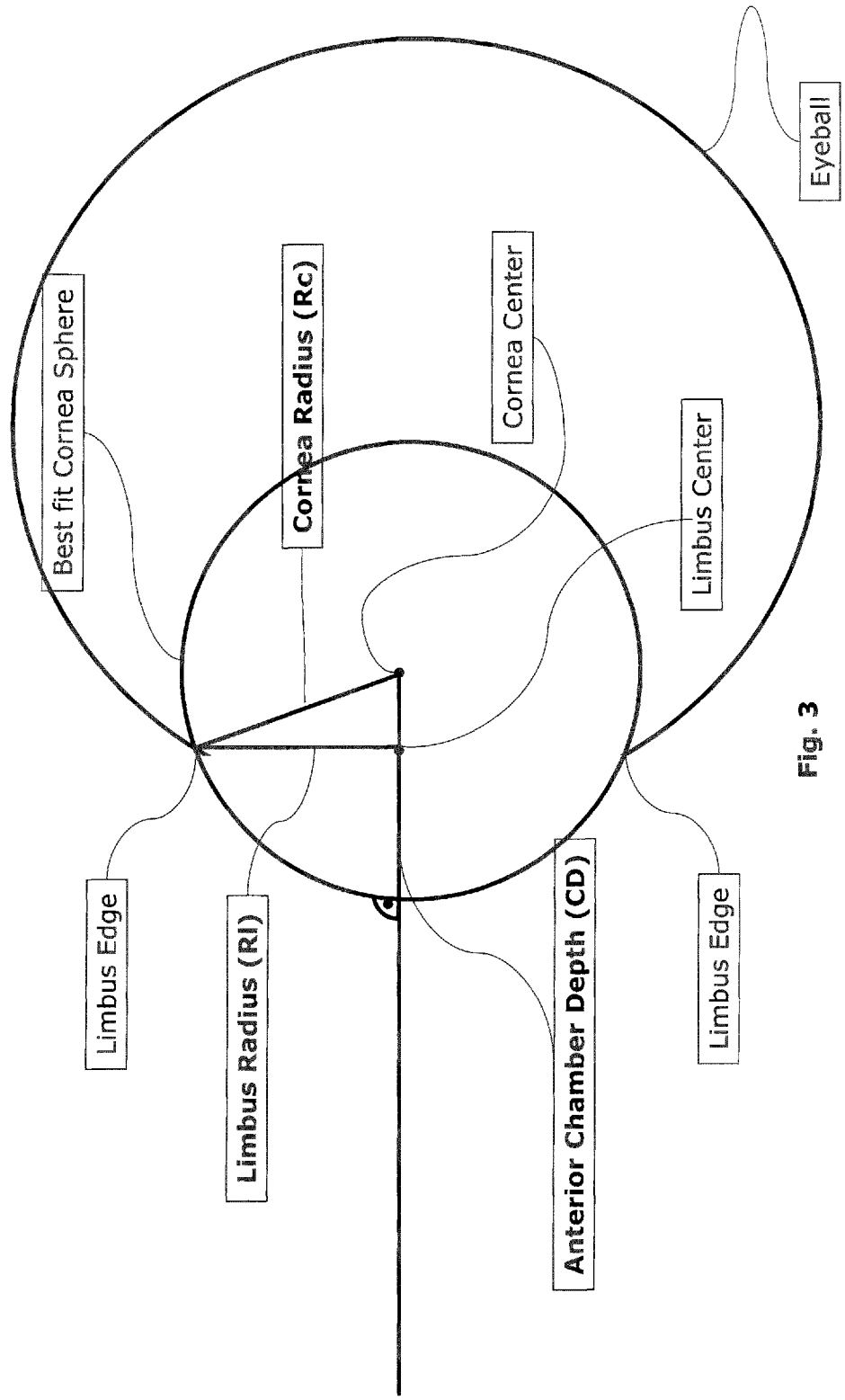

The radius Rc of the best fit sphere resembling the cornea surface is the mean of flat and steep axis as determined from the k-readings. Assuming the limbus with radius Rl to be a circle of latitude on the best fit cornea sphere with radius Rc, an approximation of the corneal chamber depth CD can be derived by $CD = Rc - \sqrt{Rc^2 - Rl^2}$. This is schematically illustrated in FIG. 3.

6) Intersection of LOS or Visual Axis with Cornea Surface

The intersection is a valid reference point for implanting corneal inlays and for centering laser treatments. It can be approximated by intersecting the best fit cornea sphere with the LOS.

The lateral coordinates of the center of this sphere Xc and Yc are well approximated by the center of the corneal reflections of the ring of LEDs. The Z coordinate of the sphere center is modeled by $Zc = Zp - CD + Rc$.

Using simple vector algebra the intersection between the LOS and the sphere defined by its center [Xc,Yc,Zc] and its radius Rc can be calculated.

Figure 4:
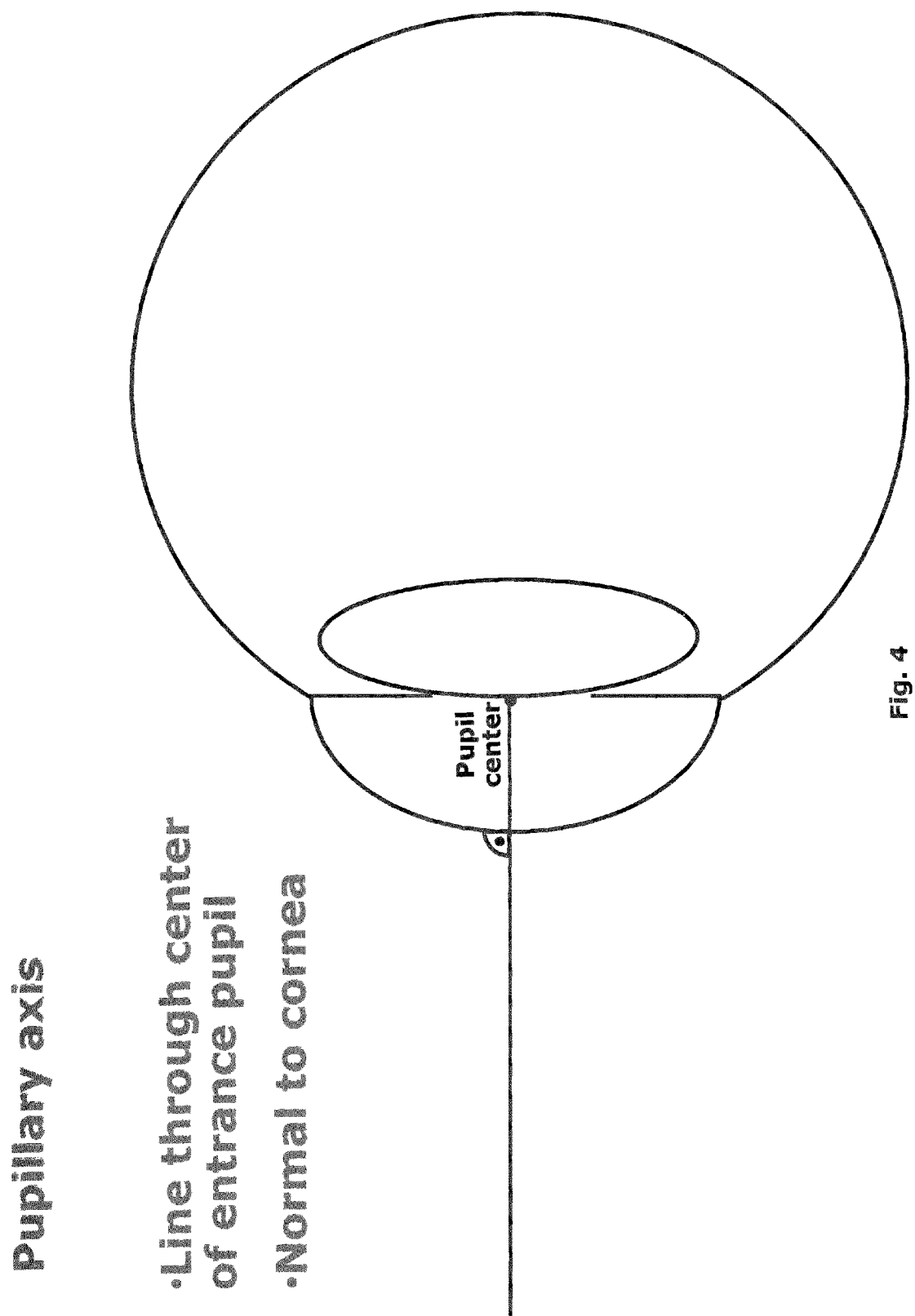
Figure 5:
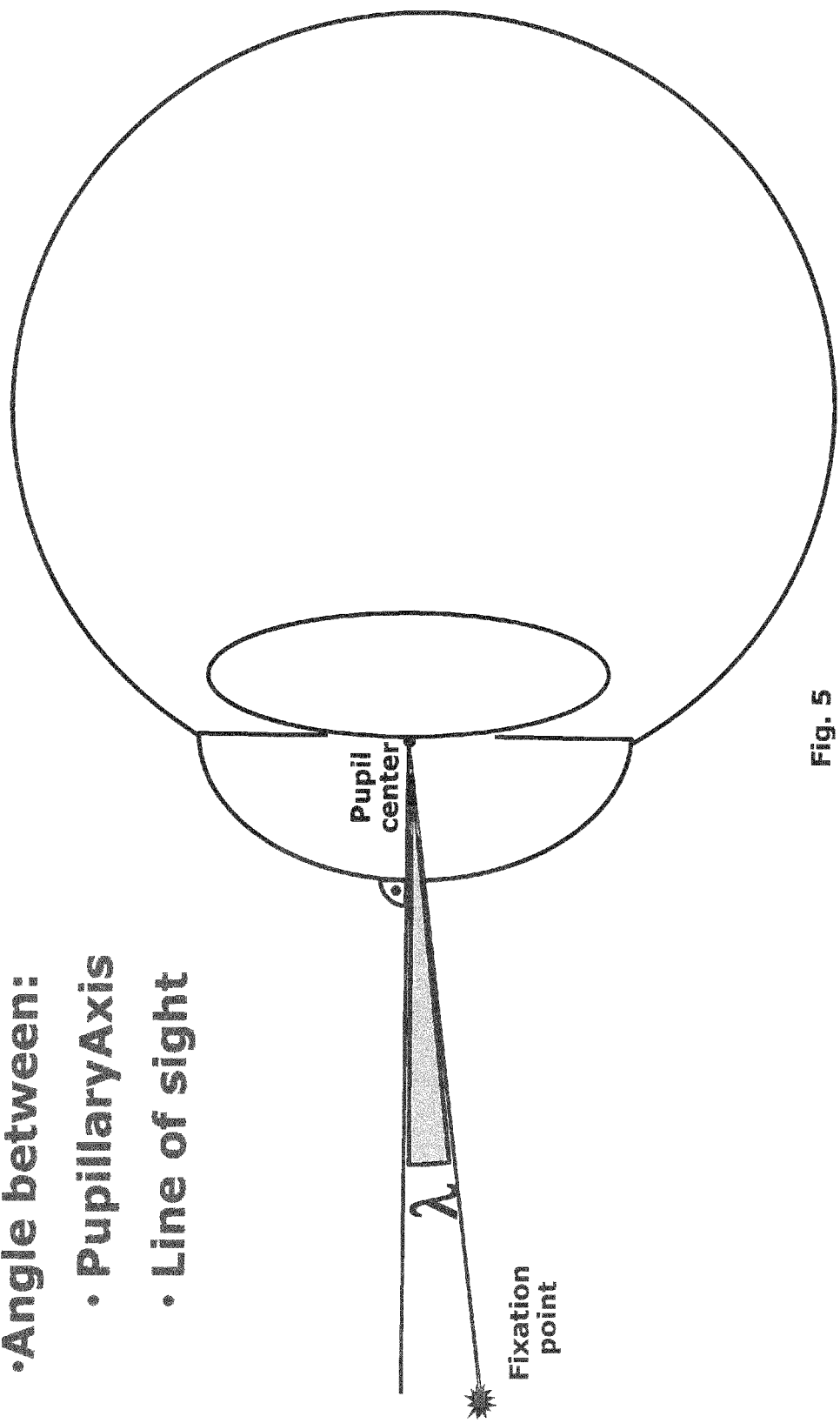

Implicitly this intersection is also a representation for the often cited angle kappa or lambda. In the literature angle kappa is referred to as the angle between the Visual Axis (VA see definition in section below) and the Pupillary axis (PA) connecting the pupil center [Xp,Yp,Zp] to the cornea center [Xc,Yc,Zc]. The PA is therefore a normal to the cornea surface. This and its determination is illustrated in FIG. 4. The determination of the PA may in one embodiment the carried out as follows:

1. Detect Pupil center in image to get pupil XY
2. Detect corneal reflections
3. Calculate cornea center XYZ and Cornea radius from CRs
4. Detect Limbus size in image
5. Use limbus size and cornea radius to calculate anterior chamber depth
6. Use anterior chamber depth and cornea center XYZ to calculate pupil Z
7. PA is vector through pupil XYZ and cornea center XYZ Since an objective measurement of the VA is not trivial often the LOS is used instead, its determination has already been described above. The angle between PA and LOS is referred to as angle lambda in the literature (see FIG. 5). In practical terms lambda=kappa (up to 0.2°).

Figure 6:
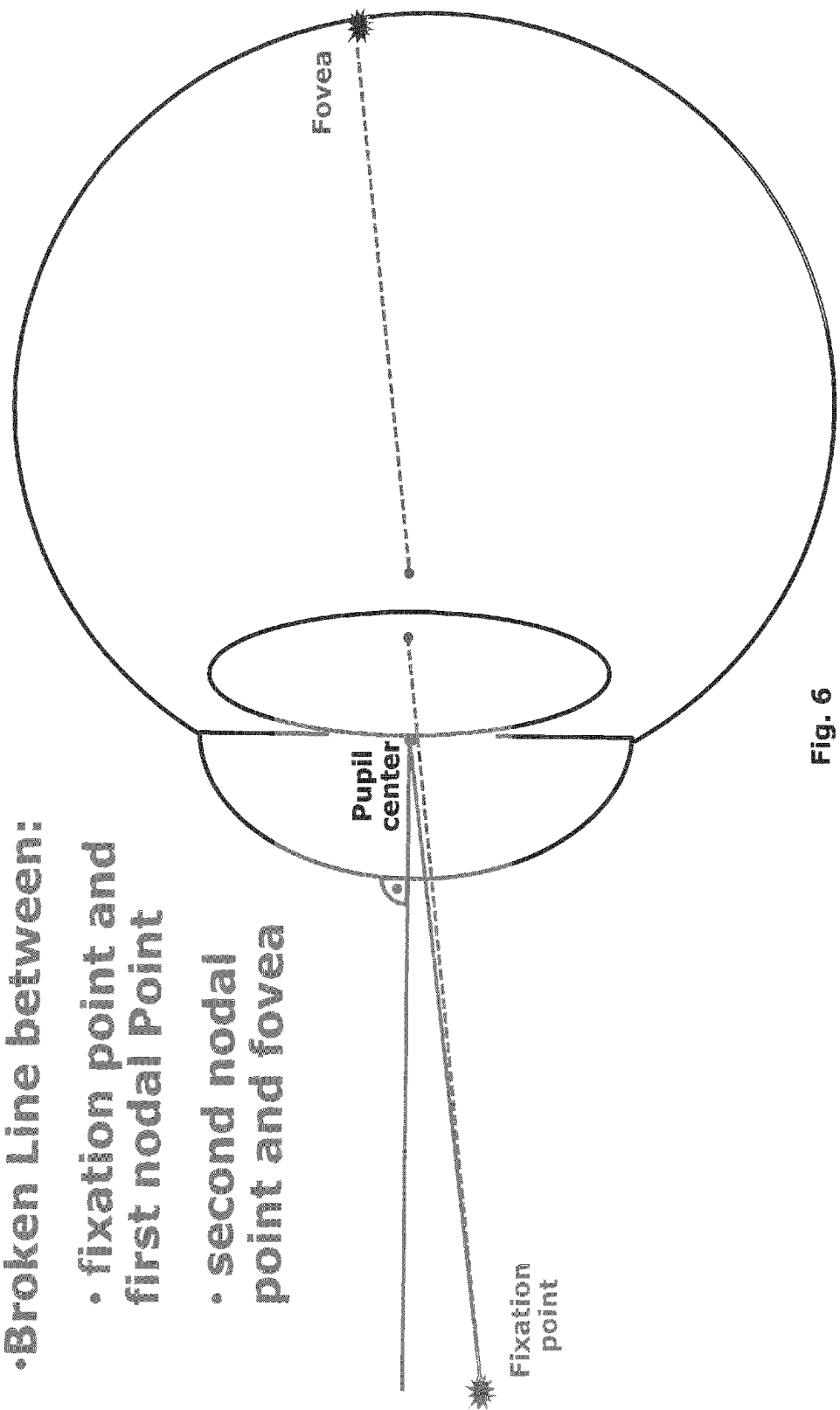
Figure 7:
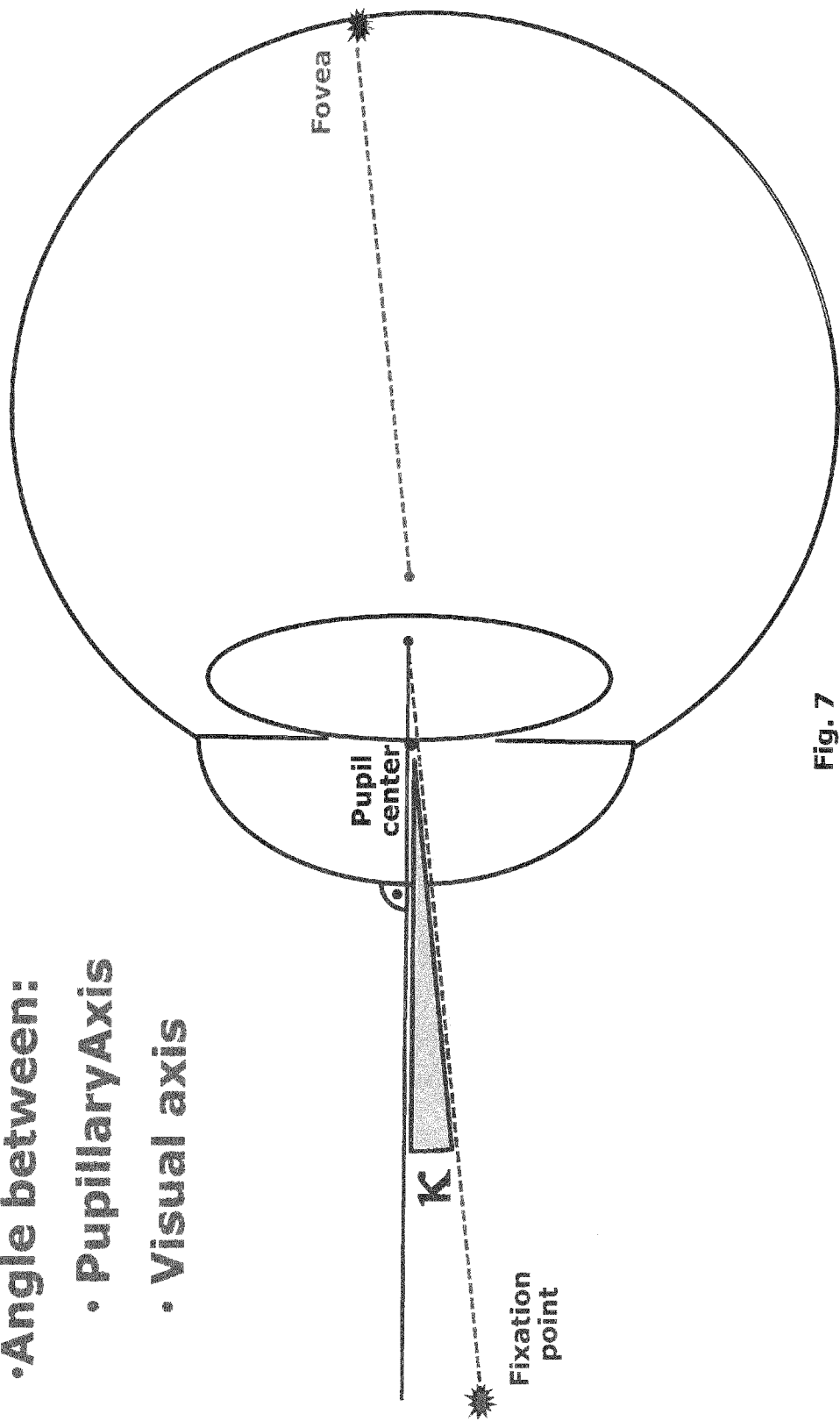

However, according to one embodiment the actual visual axis may be determined. For that purpose it is in one embodiment assumed that the cornea center matches with the first nodal point. Then the visual axis can be determined as the line connecting the fixation point and the center of the cornea. This is illustrated in FIG. 6. FIG. 7 then illustrates the determination of the angle kappa. The determination in one embodiment may be carried out using the following steps:

1. Detect corneal reflections
2. Calculate cornea center XYZ and Cornea radius from CRs
3. Use model assumption cornea center=1st nodal point
4. Use given XYZ coordinates of fixation target
5. VA is vector through 1st nodal point XYZ and fixation target XYZ 7) OD/OS Classification:

Another parameter that can be derived from images acquired with the RD is whether the current image shows a left or a right eye. This parameter is rather interesting for usability purposes and gross error prevention.

It is well known in the literature that the Visual Axis (VA) (ray of light that connects the fixation point with the fovea through the first and second nodal point of the eye) has an inclination towards the nasal side compared to the Optical Axis of the Eye (OAE) (see image below). The angle between the OAE and the VA is referred to as angle ALPHA in the literature and has a magnitude of about 5°.

The OAE is the best fit line through the centers of curvature of the best fit spheres to the refractive surfaces of the eye. The refractive surfaces are the front and back surface of the cornea and the front and back surface of the lens. By centering the patient's eye in the camera image and by asking the patient to fixate on the target, the patient roughly aligns the VA to the Optical Axis of the Camera (OAC). Hence the OAE has an angle of about 5° to the OAC. The center of the corneal reflection(s) resembles a very good approximation of the image position of the cornea center which by definition of the OAE lies on, or very close to the OAE.

A new aspect utilized in this embodiment is that an axis connecting the limbus center and the cornea center, which will be referred to as Limbus Axis (LA), also provides a very reliable and stable reference to quantify the inclination of the VA towards the nasal side. The OD/OS classification based on the cornea center and the limbus center is reliable since:

The patient is fixating and aligns the VA to the OAC.

Both, the center of the cornea and the center of the limbus do lie on the LA and very close to the OAE.

The limbus center is always closer to the camera than the cornea center.

The VA points to the nasal side.

Figure 8:
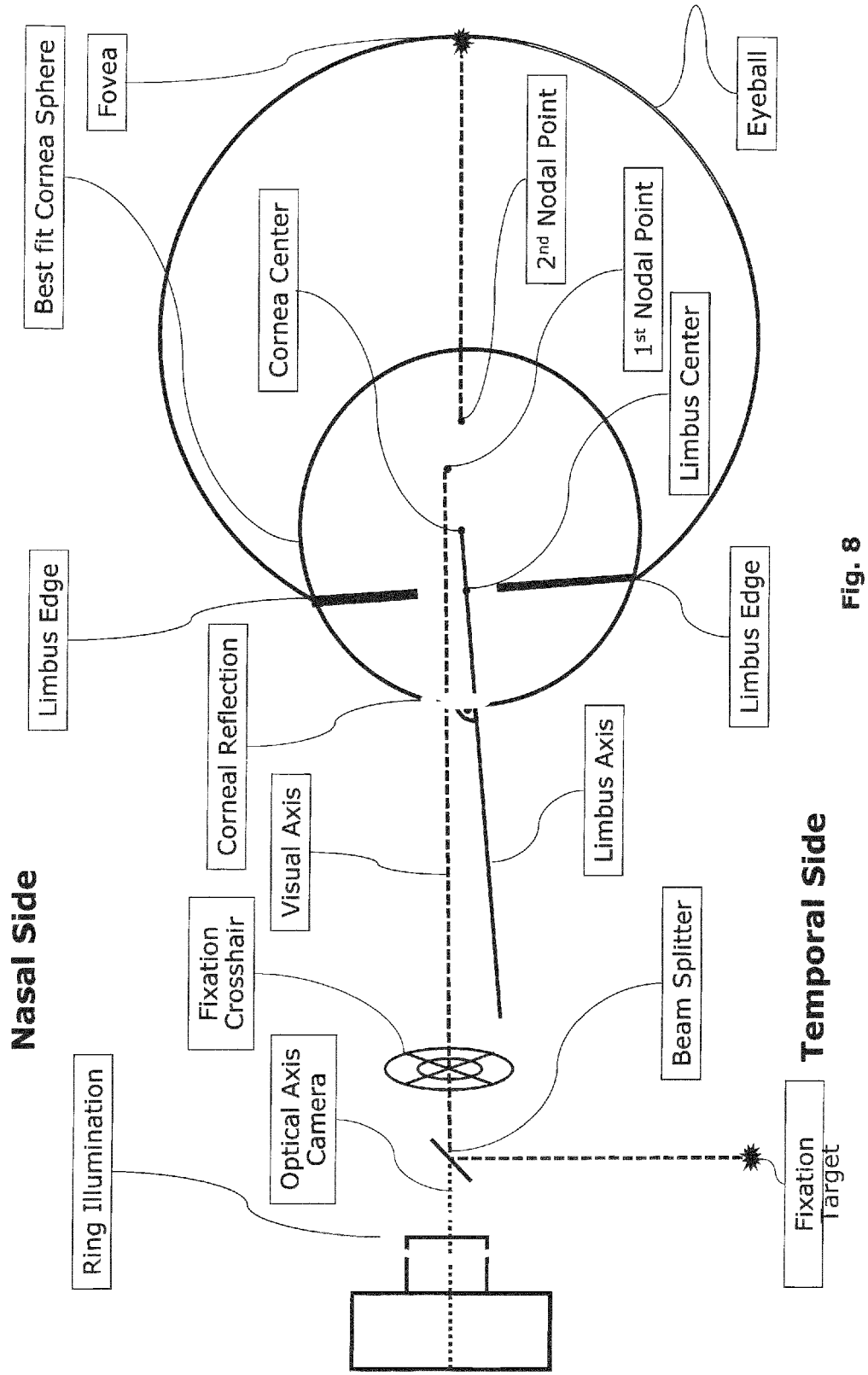

This is illustrated in FIG. 8.

Figure 9:
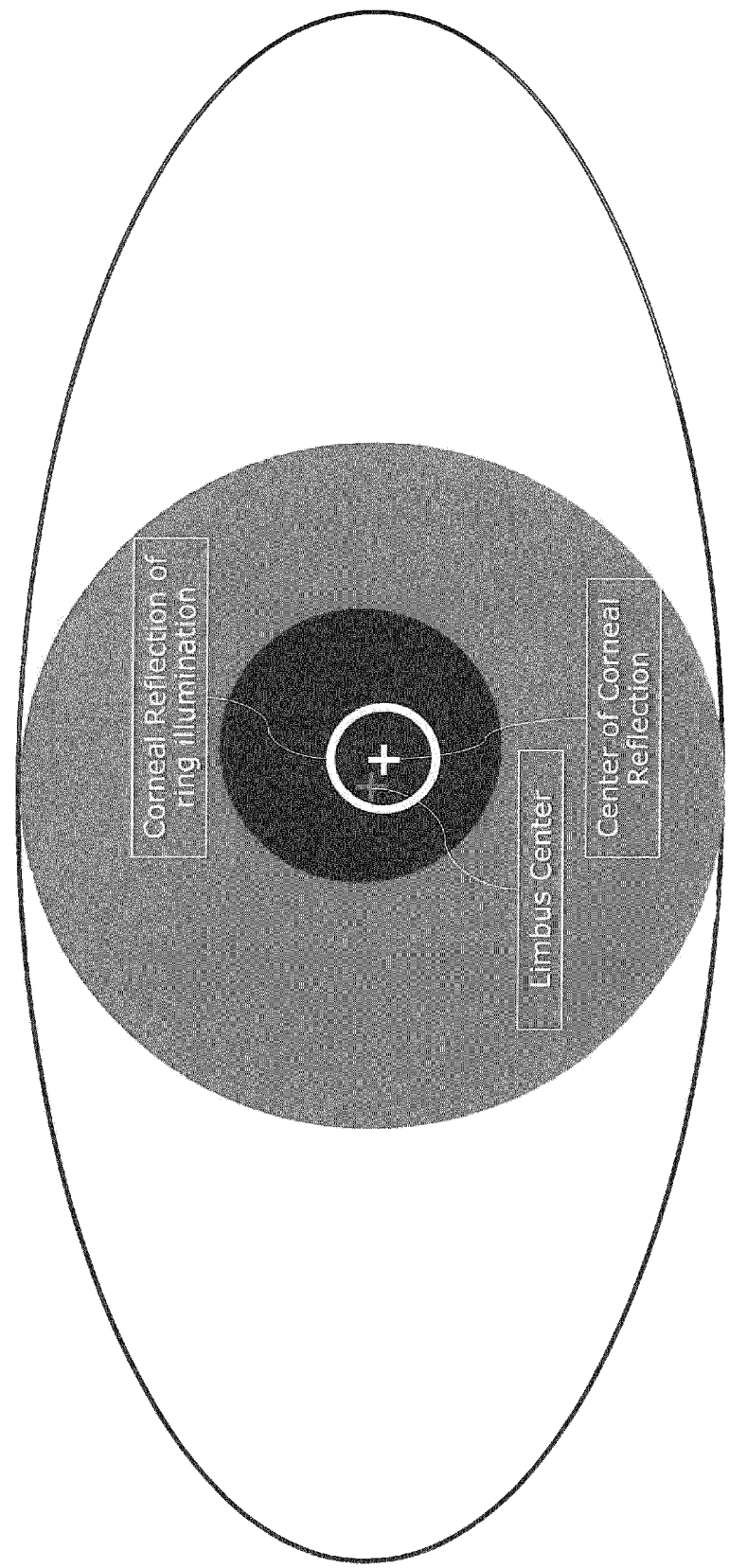

It follows that in the camera image the cornea center appears left of the limbus center for the left eye and right of the limbus center for the right eye. This is illustrated in FIG. 9.

In the following there will be explained in somewhat more detail how according to one embodiment the eye motion is measured and the coordinated transformation is determined.

According to one embodiment there is determined the relative eye motion with respect to the reference measurement in 6 degrees of freedom. This is the basis for the link between measurements taken during different measurement sessions that may be minutes, days, months or years apart and may be performed on different diagnostic devices. U.S.

Pat. No. 7,600,873 B2 teaches how to utilize eye features like sclera blood vessels, pupil, limbus, iris features and/or corneal reflections for recovering eye motion in 6 degrees of freedom.

The 6 recovered parameters (translations in X, Y, Z and rotations around X, Y and Z-axes) describe a transformation—a spatial similarity transformation—that may be applied to any derived coordinates on the eye or in the eye. In one embodiment the same feature based approach as described in U.S. Pat. No. 7,600,873 B2 is used.

In the foregoing there have been described embodiments where eye parameters which relate to the shape or location of the eye or its optical properties are determined by using an image of the eye and of corneal reflections of a ring shaped illumination source and eye model which represents the eye itself by a geometrical model. In addition to the corneal reflections which are directly determined, one or more of such "further" eye parameters are determined using the eye model: the determined setting of the camera, the illumination source, and in some embodiments also comprises a known fixation point. These parameters are determined over multiple sessions to monitor and record the change of these parameters over time between different sessions by using a coordinate transformation which is based on the determination of the eye movement in six dimensions. It should be noted that the described "further parameters of the eye" may be measured alone or in an arbitrary combination in a measurement session.

Now embodiments will be described in which further surgical eye parameters, e.g. eye parameters which relate to implants are determined, such as e.g. the orientation and/or position of implants. These parameters may be measured in addition to the "further eye parameters" described before, or they may be measured alone or alternatively to them during one session Like with the "further eye parameters" described before these implant related parameters are measured during multiple sessions which are temporally spaced and between which the patient—and the eye—typically has moved. Also for these "implant-related parameters" the movement of the eye between different sessions in six degrees of freedom is determined to obtain a transformation which enables the transformation of the measured parameters into a consistent coordinate system which is consistent over the multiple sessions. This enables then to compare and monitor how these implant related parameters change over time which is very important information for the doctor. For that purpose these parameters may be compared with their corresponding implant-related parameters as determined in previous sessions, or with the "further" non-implant related parameters. The parameters of different sessions (non-implant related ones, implant related ones or any combination of both of them) which are to be compared may be visualized within the same image by using the coordinate transformation obtained by the eye movement determination which enables the doctor to judge the development of these parameters over time in a consistent coordinate system which compensates or eliminates the effect of the movement of the eye between different sessions.

Other surgical eye parameters which may be determined are e.g. the location and/or contour of corneal or limbal or scleral incisions. These parameters may have a relation with an implant (and may therefore in some embodiments be "implant-related parameters"), however, there are also surgical techniques like e.g. the LRI (limbus relaxation incision) where incisions are made without an implant being placed. For such surgical techniques the relevant parameters like the location and/or contour of corneal or limbal or scleral incisions may be determined over multiple sessions.

In the following embodiments will be described where implant-related eye parameters are determined. The implant related eye parameters may in one embodiment belong to one of two categories, the first one being the position and/or orientation of an implant in the eye, and the second one being related to the position and/or orientation of the rhexis.

Both may also be combined, for example the position of the rhexis and the location or shape of a lens implant.

In the following some embodiments will be described in more detail.

First some embodiments measuring the orientation and/or position of implants in the eye will be described.

a) Location of the Implant Markings in the Eye (Toric Marks or Multifocal Marks)

Different eye implants like toric IOLs or Multifocal IOLs do have distinct markers. According to one embodiment these markers are automatically detected using image processing techniques, e.g. edge detection and/or template based feature detection. This way basically any man made feature on or in an inlay or implant can be detected and their lateral position in the eye can be monitored over time.

Figure 10:
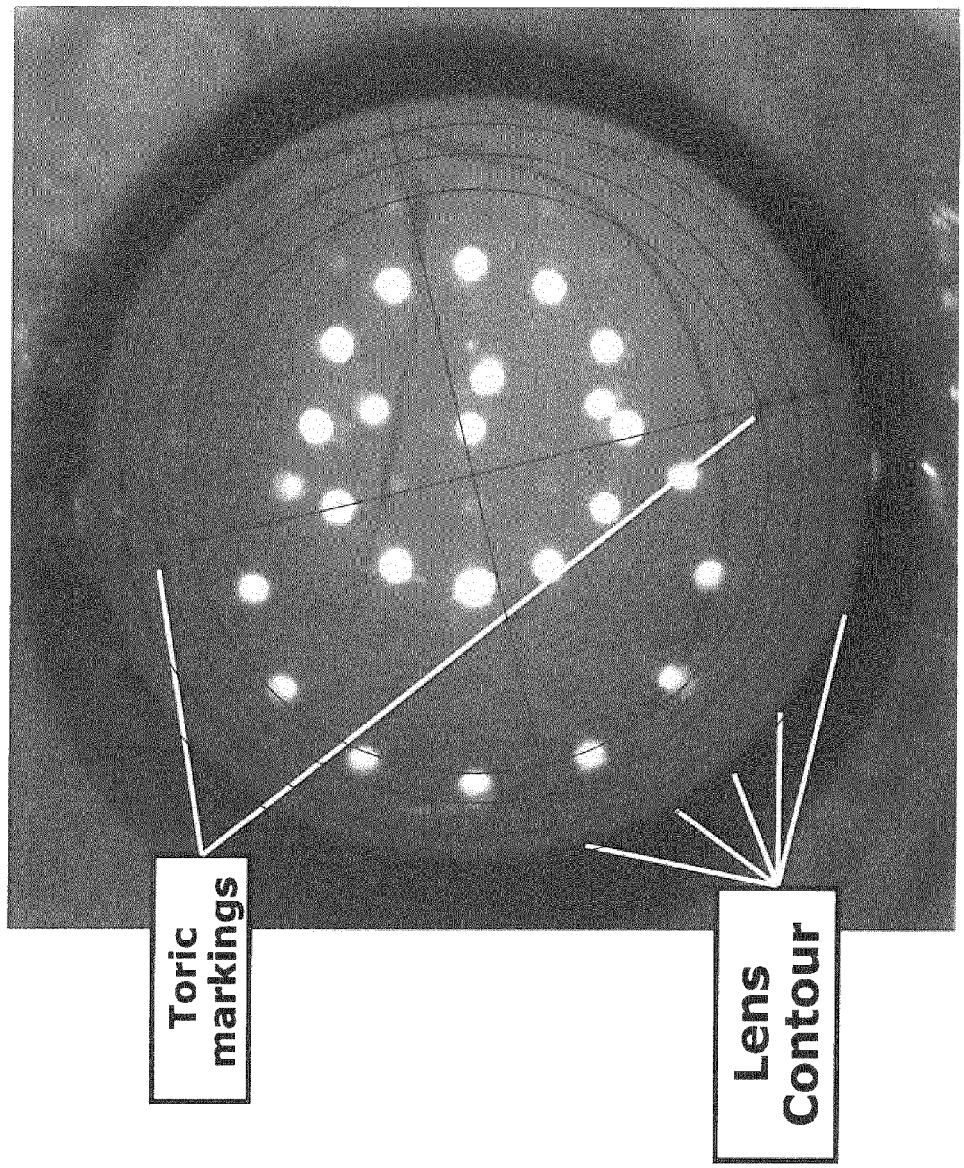

In the case of toric IOLs e.g. the markings do show either the steep or the flat axis of the toric lens and they are used by the surgeon to accurately align the lens in the eye. In case of multifocal IOLs, concentric rings in the lens are visible which are used by the surgeon to laterally position the lens. FIG. 10 illustrates these markings and their determination in an eye image.

b) Cyclotorsion Orientation of Implants

As mentioned above the cyclotorsional orientation of a toric IOL can be recovered by detecting the toric marks on the lens that resemble either the flat, the steep or implantation axis of the IOL (depending on the type). This is also illustrated in FIG. 10 by the axis that is overlaid over the steep or the flat axis of the toric lens and which have been determined based on the location of these markings.

c) Roll and Tilt Orientation of Implants

The exact shape and refraction of the implant (for example an IOL) is known. This allows for a model based ray tracing approach to recover roll, tilt orientation and lateral position of the IOL in the eye, which is used according to one embodiment to determine the roll and tilt of an implant.

Figure 11:
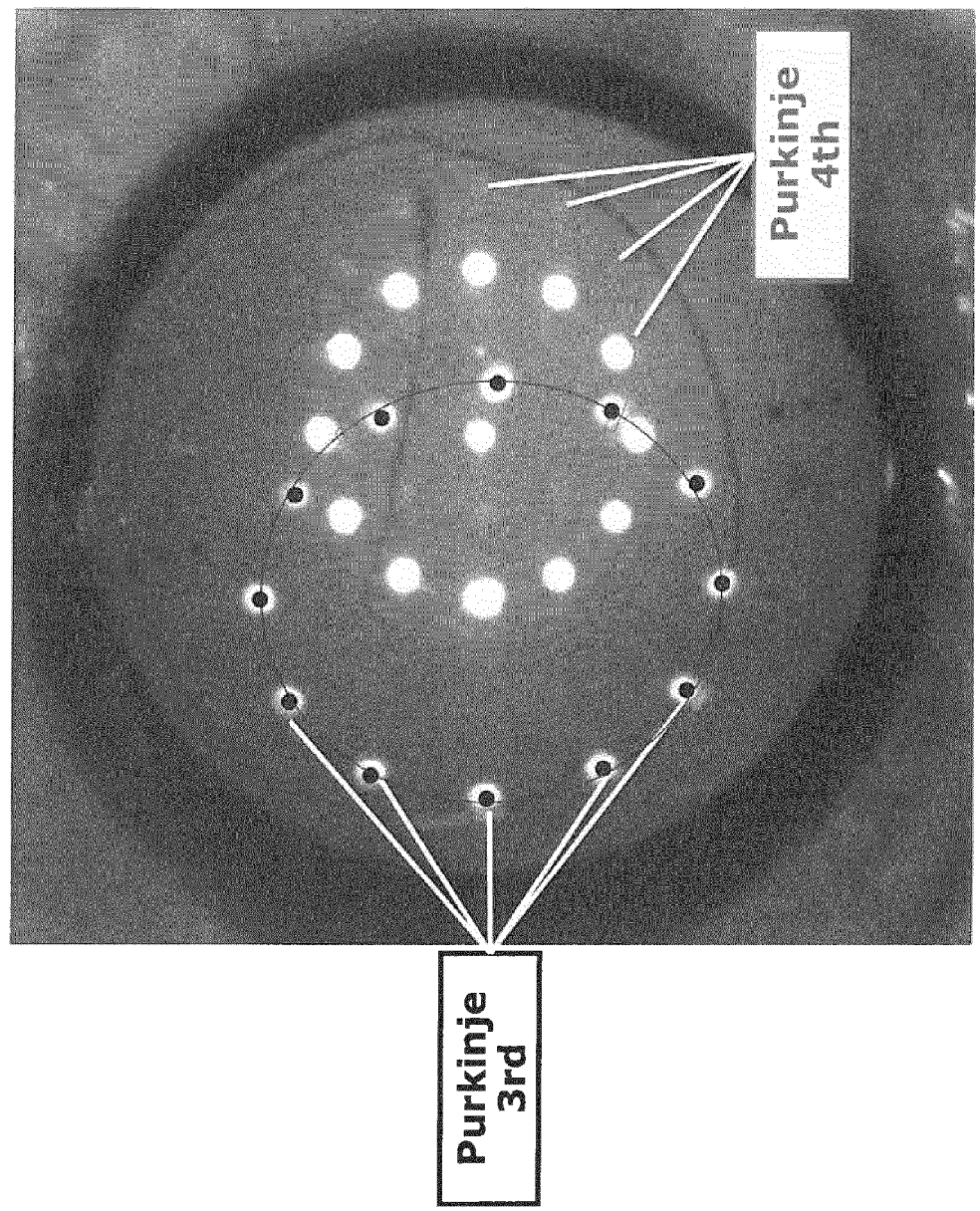
Figure 12:
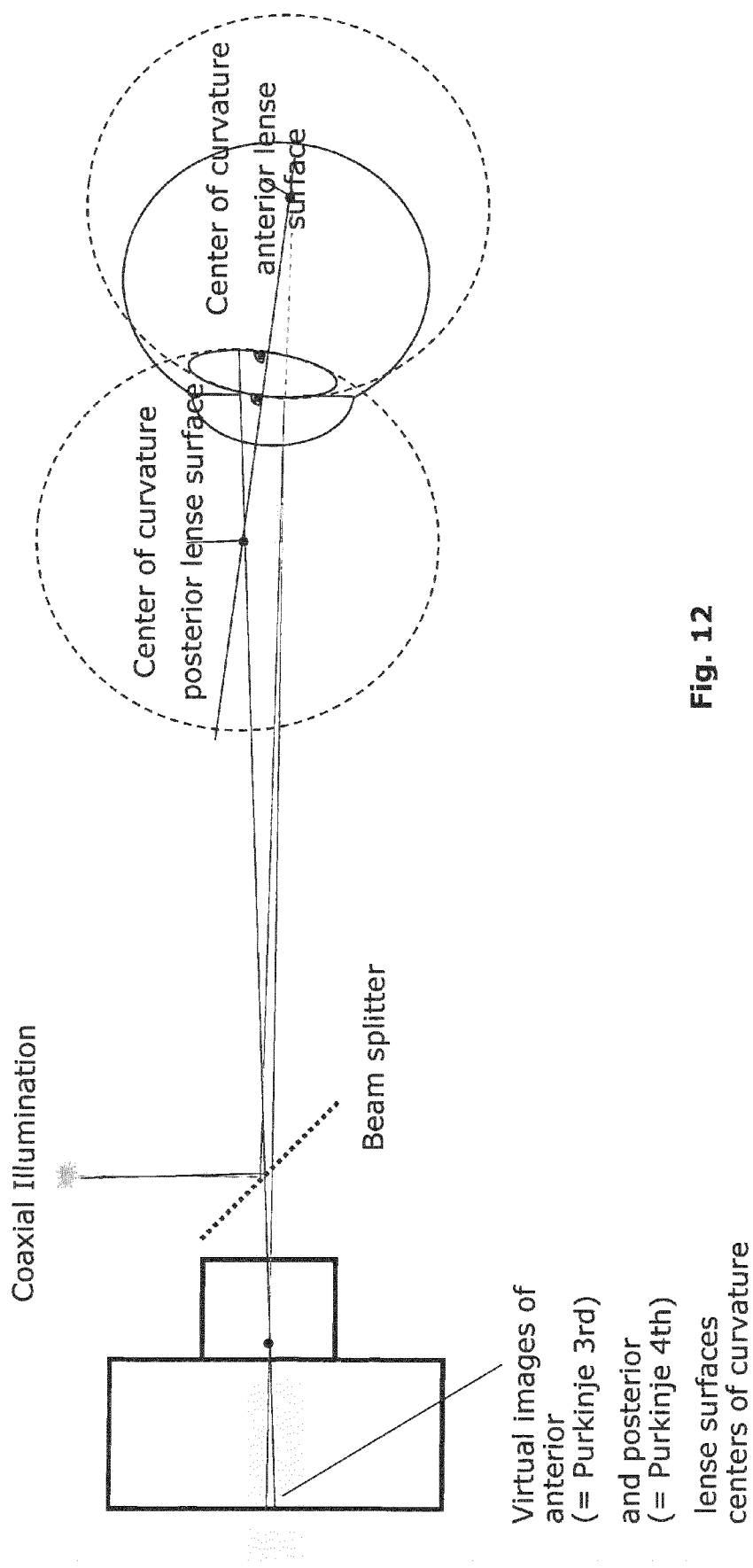

The known coaxial illumination system of the RD creates reflections on the front side and backside of the IOL (3rd and 4th order purkinje images), as illustrated in FIG. 11. If the lens rolls or tilts, the 3rd and 4th order purkinjes will move with respect to each other. In the special case in which the 3rd and 4th order purkinje superimpose, the optical axis of the IOL is aligned with the optical axis of the camera. The locations of the 3rd and 4th order purkinje images can be used to determine the roll and tilt of the implant, e.g. by using an approach as described in "Reproducibility of intraocular lens decentration and tilt measurement using a clinical Purkinje meter", Yutaro Nishi et. al. J Cataract Refract Surg 2010; 36:1529-1535 Q 2010 ASCRS and ESCRS. Reference is in this context also made to FIG. 12 which illustrates the determination of the determination of the orientation of the intraocular lens based on the 3rd and 4th order purkinje reflections. Like in the usage of the reference device before a circular illumination is applied which is coaxial with the camera axis. The orientation determination method in one embodiment then may comprise the following steps:

1. Detect center of purkinje 3rd
2. Detect center of purkinje 4th

3. Use the IOL shape information including distance between anterior and posterior centers of curvature=DCC 4. Recover optical axis of lens using distance between 3rd and 4th purkinje centers, camera parameters and DCC.

d) Implant Contour

Figure 13:
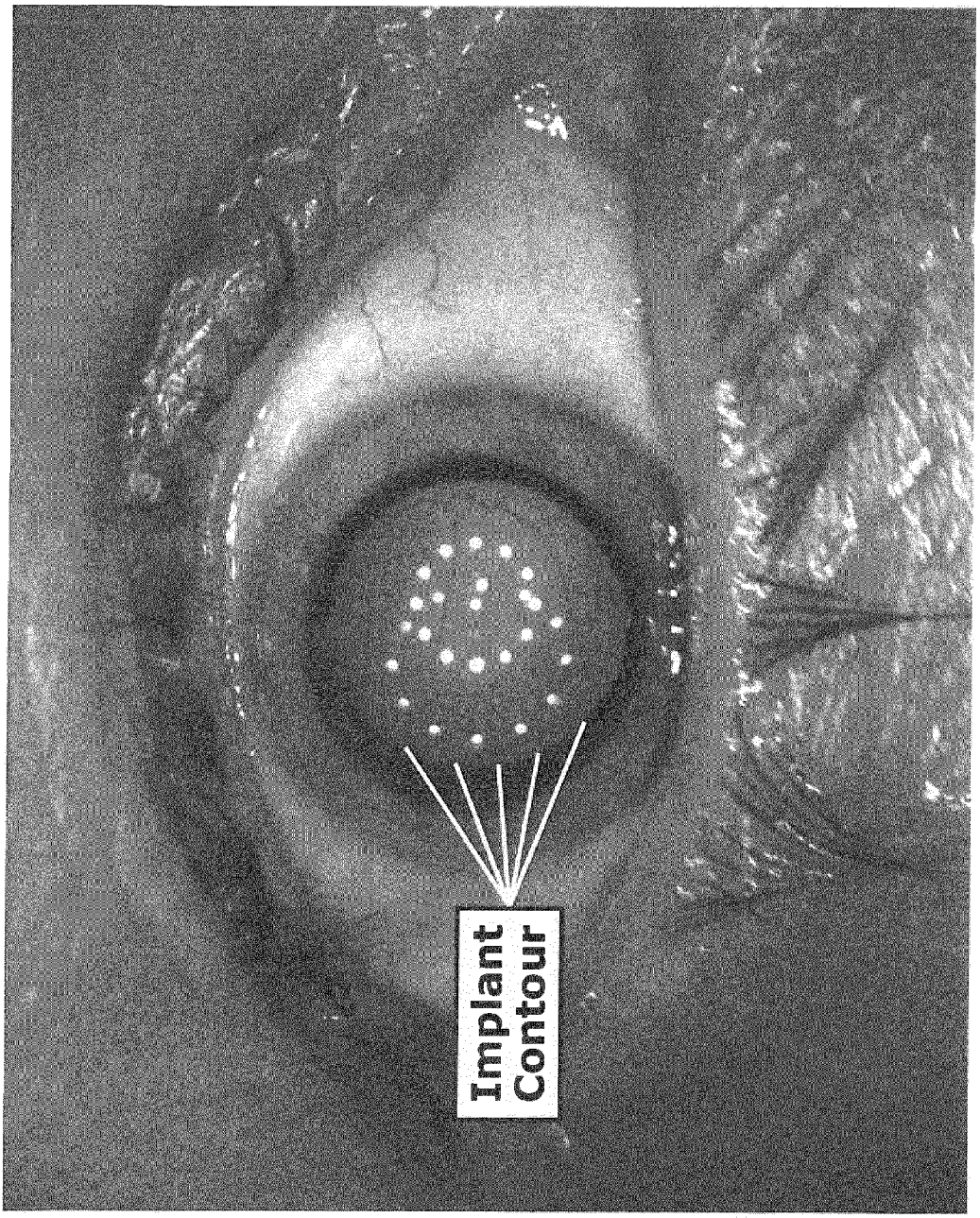

The implant contour is clearly visible in the RD images if it is not obstructed by iris tissue. The unobstructed parts can be recovered with standard image processing techniques like edge detection. By fitting a known edge shape model of the inlay in the detected contour parts or detected implant markings in one embodiment it is also possible to recover the obstructed parts of the inlay contour. This is illustrated in FIG. 13.

e) XY-Position of the Implant Center

Since the shape of the implant is known a variety of techniques can be used to recover the lateral position of the implant center. According to one embodiment, detecting the location of the implant marks, using the implant contour to recover the center or the ray tracing approach described under c) can be used.

f) Location of the Implant Haptics in the Eye

For detecting the haptics according to one embodiment the same approach as for the implant contour is employed. The haptics have a well defined shape and are basically part of the implant contour. Now some embodiments where the implant related parameter relates to the rhexis will be described.

g) Contour

Figure 14:
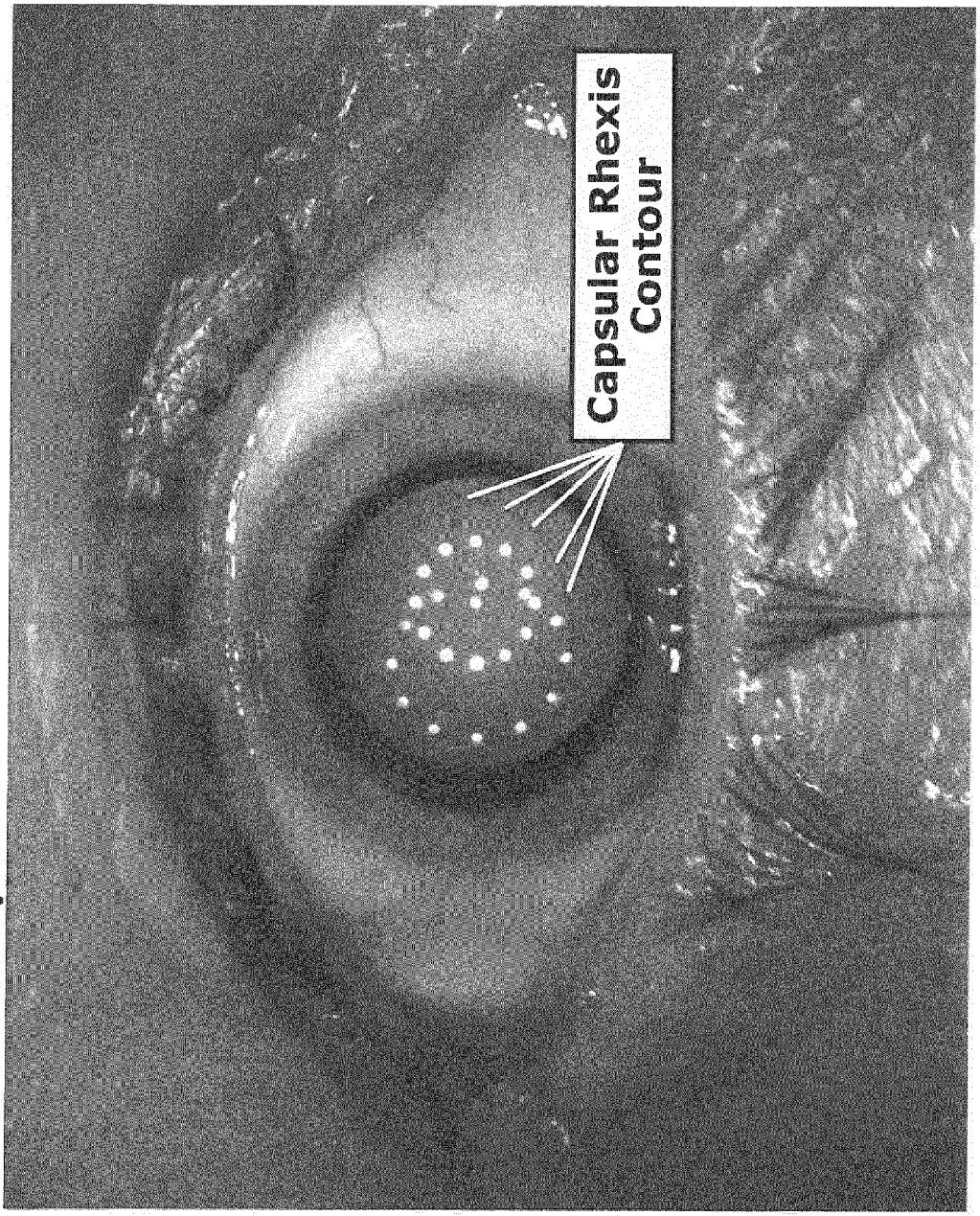

Using edge detection techniques can recover the clearly visible rhexis in the RD images. Alternatively it can also be measured by manually selecting a polygon that best resembles the contour of the rhexis. The rhexis contour is illustrated in FIG. 14.

h) Diameter

The diameter can be retrieved by least squares fitting of a circle or ellipse into the contour of the rhexis.

i) XY Position in the Eye

The XY position of the rhexis according to one embodiment can be defined and determined as the center of the best fit circle or ellipse into the contour of the rhexis.

j) Overlap with Lens

Figure 15:
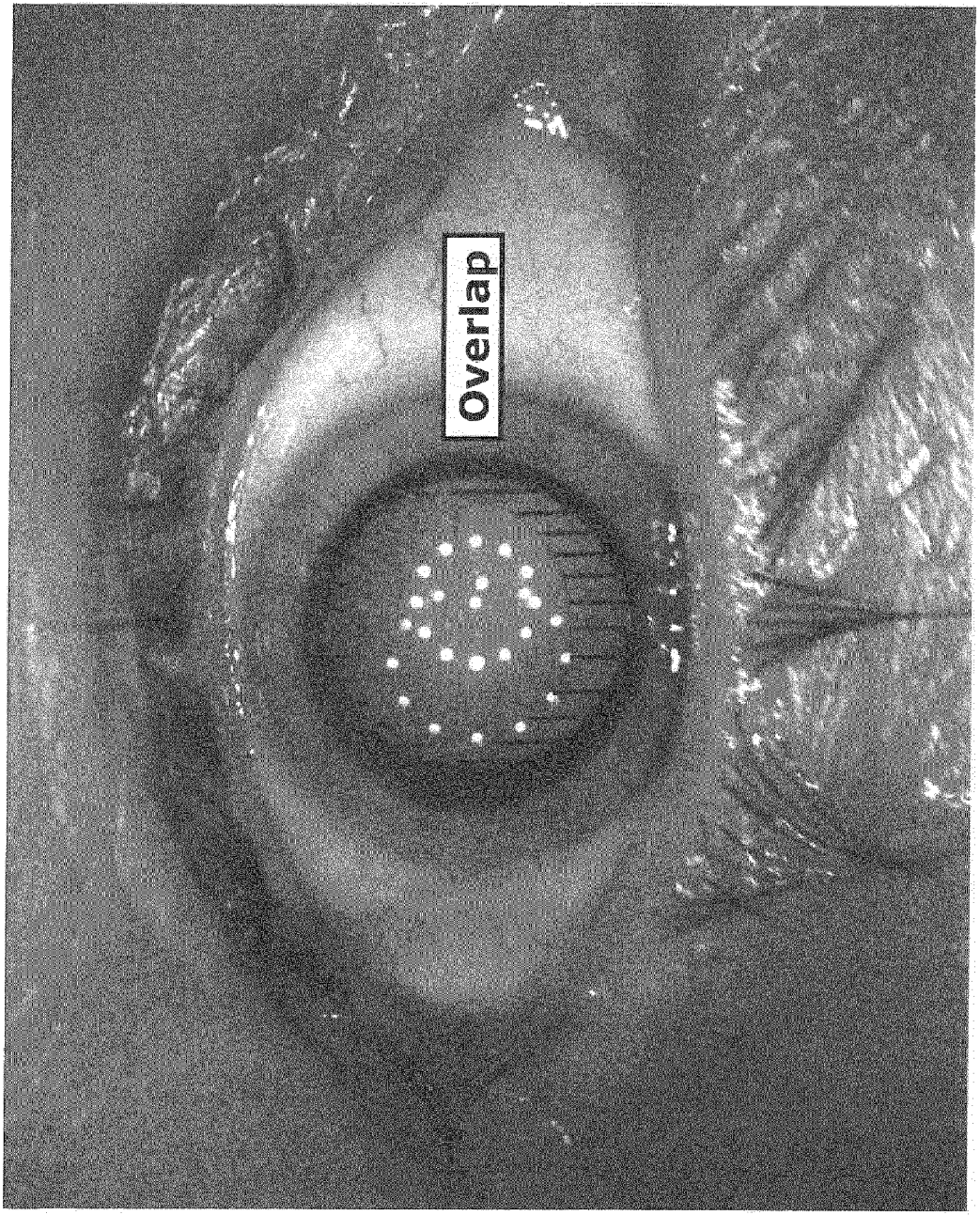

Superimposing the contour of the rhexis with the contour of the lens. The area inside the contour of the lens implant and outside the contour of the rhexis is the overlap. This is illustrated in FIG. 15. This is an important measure to determine how stable the lens implant is in the eye. If the overlap on one side becomes too small chances are the implant will be instable.

In the foregoing several embodiments of the invention have been described which come along with several advantages.

E.g. by being able to spatially transform all measurements to an initial reference frame (or any arbitrary reference frame chosen in one of the sessions), any influence due to a potential eye motion can be eliminated and all measured parameters can be normalized with respect to the reference frame.

This allows a continuous monitoring of all measured eye parameters. A truly measurement driven approach to investigate the post surgery behavior of implants and surgical cuts in the eye becomes possible without being limited in accuracy to the amount of eye motion inherently present in all multi session diagnostic data collection trials.

The skilled person will recognize that the modules or units of the embodiments of the invention described before may be implemented by software or hardware or a combination thereof. In particular, the hardware may comprise a camera and a computer which is programmed to perform the tasks as described in connection with the embodiments of the invention, in particular such tasks as image processing to determine eye parameters or displaying for displaying eye parameters in addition to the eye image.

What is claimed is:

1. An apparatus for monitoring one or more surgical parameters at least one surgical parameter of an eye over multiple sessions which are temporally spaced apart and between which the eye of a patient can have moved, said apparatus comprising:
 a camera for taking one or more images of the eye;
 an image processing computer configured to:
  determine during a first session, said at least one surgical parameter of the eye and its coordinates based on the image taken by said camera in the first coordinate system;
  determine during a second session temporally spaced apart from said first session, said at least one surgical parameter of the eye and its coordinates based on the image taken by said camera in a second coordinate system;
  determine an eye motion in six degrees of freedom between said first and said second session and for determined a coordinate transformed based thereon;
  transform based on said determined eye motion said at least one surgical parameter of the eye and its coordinates from said first coordinate system into said second coordinate system;
  quantify or visualize a change of said at least one surgical parameter of the eye and its coordinates between said first and said second session based on said surgical eye parameter and its coordinates measured during said second session and said transformed surgical eye parameter and its coordinates measured during said first session, wherein said surgical eye parameters are one or more of the following:
   implant-related parameters of the eye which are based on an implant which has been surgically placed in the eye of a patient; or
   a location or contour of corneal or limbal or scleral incisions.

2. The apparatus of claim 1, wherein said implant related eye parameter comprises one or more of the following:
 an orientation or position of the implant in the eye;
 a location or the contour of a rhexis;
 an overlap of the rhexis with a contour of the implant.

3. The apparatus of claim 1, wherein said image processing computer configured to quantify or visualize the change of said at least one surgical eye parameter is also configured to:
 display said least one surgical eye parameter measured during said second session and said transformed surgical eye parameter measured during said first session in the image of the eye taken during said second session; or calculate a difference between said surgical eye parameter measured during said second session and said transformed surgical eye parameter measured during said first session and visualize said difference in said image of the eye taken during said second session.

4. The apparatus of claim 1, wherein said first session is one of:
 a pre-surgery session and said second session is an intra surgery session or a post surgery session, an intra-surgery session and said second session is a post surgery session, and
a post-surgery session and said second session is another post surgery performed at a later time.

5. The apparatus of claim 1, wherein said image processing computer is configured to:
measure and record said at least one surgical eye parameter during multiple sessions over time in order to record the change of said at least one surgical eye parameter over time.

6. An apparatus for monitoring at least one surgical parameter of an eye over multiple sessions which are temporally spaced apart and between which the eye of a patient can have moved, said apparatus comprising:
a camera for taking one or more images of the eye;
an image processing computer configured to:
determine during a first session, said as least one surgical parameter of the eve and its coordinates based on the image taken by said camera in a first coordinate system;
determine during a second session temporally spaced apart from said first session said at least one surgical parameter of the eye and its coordinates based on the image taken by said camera in a second coordinate system;
determine an eye motion in six degrees of freedom between said first and said second session and for determining a coordinate transformation based thereon;
transform based on said determined eye motion said at least one surgical parameter of the eve and its coordinates from said first coordinate system into said second coordinate system;
quantify or visualize a change of said at least one surgical parameter of the eve and its coordinates between said first and said second session based on said surgical eye parameter and its coordinates measured during said second session and said transformed surgical eye parameter and its coordinates measured during said first session, wherein said surgical eye parameters are one or more of the following:
implant-related parameters of the eye which are based on an implant which has been surgically placed in the eye of a patient; or
a location and/or or contour of corneal or limbal or scleral incisions;
the apparatus further comprising:
an illumination unit for illuminating the eye by a ring-shaped light pattern to generate corneal reflection, said illumination unit being preferable located such that the center of the ring is coaxial with the optical axis of the camera;
the image processing computer also configured to:
determine during said first or said second session the location of the corneal reflections in the image of the eye;
determine during said first or said second session based on said determined location of the corneal reflections, at least one further parameter of the eye and its coordinates in said first or second coordinate system based on a geometrical model representing the eye as a spherical eyeball having a spherically shaped cornea mounted thereon;
visualize said at least one further parameter of the eye together with said at least one implant related eye parameter in the same image after having transformed its coordinates based on the eye motion between said first and said second session so that the motion of the eye is compensated.

7. An apparatus for monitoring at least one surgical parameter of an eve over multiple sessions which are temporally spaced apart and between which the eve of a patient can have moved, said apparatus comprising:
a camera for taking one or more images of the eye;
an image processing computer configured to:
determine during a first session, said at least one surgical parameter of the eve and its coordinates based on the image taken by said camera in a first coordinate system;
determine during a second session temporally spaced apart from said first session said at least one surgical parameter of the eye and its coordinates based on the image taken by said camera in a second coordinate system;
determine an eye motion in six degree of freedom between said first and said second session and for determining a coordinate transformation based thereon;
transform based on said determined eve motion said at least one surgical parameter of the eve and its coordinates from said first coordinate system into said second coordinate system;
quantify or visualize a change of said at least one surgical parameter of the eve and its coordinates between said first and said second session based on said surgical eve parameter and its coordinates measured during said second session and said transformed surgical eye parameter and its coordinates measured during said first session, wherein said surgical eye parameters are one or more of the following:
implant-related parameters of the eye which are based on an implant which has been surgically placed in the eye of a patient; or
a location or contour of corneal or limbal or scleral incisions;
the image processing computer also configured to:
determine during said first or said second session, at least one further parameter of the eye and its coordinates in said first or second coordinate system based on a geometrical model representing the eve as a spherical eyeball having a spherically shaped cornea mounted thereon;
wherein said at least one further parameter is determined based on an eye model which represents the shape and location of the eye by a spherical eyeball and a cornea mounted thereon and having a spherical shape or the shape of an ellipsoid to thereby enable calculation of said at least one further parameter using a measured location of corneal reflections and said eye model.

8. The apparatus of claim 7, wherein said at least one further eye parameter comprises one or more of the following:
k-readings which define the shape of the cornea in terms of rotation ellipsoid parameters;
line of sight as the line connection the pupil center and a fixation point of known location:
corneal chamber depth;
visual axis of the eye;
determination whether the eye is the left eye or the right eye.

9. The apparatus of claim 8, wherein:
said at least one further eye parameter comprises the k-readings which are measured by determining a best first ellipse to the corneal reflections and determining the major axis, the minor axis and the orientation of the ellipse.

10. The apparatus of claim 6, wherein:
said apparatus further comprises a fixation target at known coordinates, on the optical axis of the camera, and said at least one further eye parameter comprises a visual axis which is determined as the vector connecting the cornea center and the known fixation target, where the cornea center is determined based on the location of the corneal reflections.

11. The apparatus of claim 6, wherein:
said at least one further eye parameter comprises the angle kappa between a visual axis and a pupil axis.

12. The apparatus of claim 6, wherein:
said at least one further eye parameter comprises the anterior chamber depth which is determined based on determining the radius of the limbus RI and assuming it to be a circle of latitude on the best fit cornea sphere with radius Rc which is determined based on the corneal light reflections such that the corneal chamber depth CD is derived by $CD=Rc-\sqrt{Rc^2-RI^2}$.

13. The apparatus of claim 8, wherein:
said at least one further eye parameter comprises the line of sight which is determined as the vector connecting the pupil center and said fixation point of known location, with a z-coordinate of the pupil center being determined based on a known distance between camera and eye and x- and y-coordinates of the pupil being determined based on measuring the pupil location in the image, or
said at least one further eye parameter comprises the pupillary axis being the line going through the center of the pupil and being orthogonal to the cornea surface.

14. The apparatus of claim 6, wherein:
said at least one further eye parameter comprises the determination of whether the center of the limbus or the center of the cornea to the optical axis of the camera when the patient fixates a known fixation point lying on the optical axis of the camera.

15. The apparatus of claim 6, wherein said image processing computer is configured to:
visualize an arbitrary combination of said at least one surgical parameter of the eye and said at least one or more further eye parameters determined during said first session and a possibly different arbitrary combination of said at least one surgical parameter of the eye and said at least one or more further eye parameters determined during said second session in the same image such that the eye motion between said first and second session is compensated.

16. The apparatus of claim 6, wherein:
said further parameter is an intersection point between the visual axis and the cornea surface, where the cornea radius is determined based on the location of said corneal reflections.

* * * * *